United States Patent
Eroglu (10) Patent No.: US 11,357,225 B2
(45) Date of Patent: Jun. 14, 2022

(54) COMPOSITIONS AND METHODS FOR BIOPRESERVATION

(71) Applicant: Augusta University Research Institute, Inc., Augusta, GA (US)

(72) Inventor: Ali Eroglu, Evans, GA (US)

(73) Assignee: AUGUSTA UNIVERSITY RESEARCH INSTITUTE, INC., Augusta, GA (US)

( * ) Notice: Subject to any disclaimer, the term of this patent is extended or adjusted under 35 U.S.C. 154(b) by 640 days.

(21) Appl. No.: 16/149,379

(22) Filed: Oct. 2, 2018

(65) Prior Publication Data

US 2019/0098891 A1    Apr. 4, 2019

Related U.S. Application Data

(60) Provisional application No. 62/566,701, filed on Oct. 2, 2017.

(51) Int. Cl.
| | |
|---|---|
| *A01N 1/02* | (2006.01) |
| *C12N 5/075* | (2010.01) |
| *C12N 5/071* | (2010.01) |

(52) U.S. Cl.
CPC .......... *A01N 1/0221* (2013.01); *A01N 1/0252* (2013.01); *A01N 1/0284* (2013.01); *A01N 1/0289* (2013.01); *C12N 5/0602* (2013.01); *C12N 5/0609* (2013.01)

(58) Field of Classification Search
CPC ................ C12N 5/0602; C12N 5/0609; G02F 1/136286
See application file for complete search history.

(56) References Cited

PUBLICATIONS

Simplerler et al. J. Phys. Chem. B (2006) 110: 19678-19684 (Year: 2006).*

Bhowmick, S. et al., "Desiccation Tolerance of Spermatozoa Dried at Ambient Temperature: Production of Fetal Mice", Biol Reprod, 68(5):1779-1786 (2003). (Abstract Only).
Chen, T. et al., "Beneficial Effect of Intracellular Trehalose on the Membrane Integrity of Dried Mammalian Cells", Cryobiology, 43(2):168-181 (2001). (Abstract Only).
Eroglu, Ali et al., "Successful Cryopreservation of Mouse Oocytes by Using Low Concenlalions of Trehalose and Dimethylsulfoxide", Biology of Reproduction, 80:70-78 (2009).
Puhlev, Iskren et al., "Desiccation Tolerance in Human Cells", Cryobiology, 42(3):207-217 (2001). (Abstract Only).
Rall, W.F. et al., "Ice-Free Cryopreservation of Mouse Embryos at -196 Degrees C. by Vitrification", Nature, 313 (6003):573-575 (1985). (Abstract Only).
Wakayama, T. et al., "Development of Normal Mice from Oocytes Injected with Freeze-Dried Spermatozoa", Nat Biotechnol, 16(7):639-641 (1998). (Abstract Only).
Whittingham, D.G. et al., "Survival of Mouse Embryos Frozen to -196 Degrees and -269 Degrees C.", Science, 178 (4059 411-414 (1972). (Abstract Only).

* cited by examiner

*Primary Examiner* — Susan M Hanley
(74) *Attorney, Agent, or Firm* — Smith, Gambrell & Russell; Judy Jarecki-Black; Ram W. Sabnis (57) ABSTRACT

Methods are disclosed for viable preservation of biomaterials including both prokaryotic and eukaryotic cells/materials such as human cells and tissues at subzero and suprazero temperatures. One embodiment provides a method wherein initial desiccation and subsequent cooling of the biological samples is below their glass transition temperature (Tg) to achieve a stable glassy state without exposing the biomaterials to excessive osmotic/chemical stresses for long periods of time. Another embodiment provides a method that includes combining the initial desiccation with subsequent freeze-drying to achieve a glassy state of biomaterials. Another embodiment provides a desiccation medium with low salt, high osmolyte/glass former content and desiccation of biomaterials in a spherical droplet to avoid the edge effect.

6 Claims, 4 Drawing Sheets

COMPOSITIONS AND METHODS FOR BIOPRESERVATION

CROSS REFERENCE TO RELATED APPLICATION

This application claims benefit of and priority to U.S. Provisional Patent Application 62/566,701 filed on Oct. 2, 2017, which is incorporated by reference in its entirety.

REFERENCE TO FEDERALLY SPONSORED RESEARCH

This invention was made with government support under EB018538 and HD049537 awarded by the National Institutes of Health. The government has certain rights in the invention.

FIELD OF THE INVENTION

The invention is generally directed to preservation of cells, tissues, and organisms using a combined approach of desiccation and cooling.

BACKGROUND OF THE INVENTION

As a result of recent developments in stem cell research, tissue engineering, and genetic technologies, the living cell is being established as a therapeutic tool in medicine. Biopreservation permits cell/tissue storage and transport and is fundamental to the future of these emerging technologies. Although current technologies allow successful cryopreservation of some mammalian cells, further fundamental research is needed to develop efficient, reliable and cost-effective biopreservation techniques for more complex cells and tissues such as mammalian oocytes. Successful preservation of human oocytes would be beneficial to young cancer patients who anticipate losing their germ cells as a result of cancer therapy. Furthermore, oocyte preservation is a good fertility treatment approach for other disease states such as ovarian hyperstimulation syndrome, premature ovarian failure, and polycystic ovary, as well as a preferred alternative to embryo freezing to avoid many legal and ethical issues. In addition, oocyte banking has wide ranging research and commercial applications in livestock breeding. However, cryopreservation of mammalian oocytes has proven to be challenging due to different cryoinjury mechanisms.

Current methods for long-term storage of oocytes and other cells include (1) slow freezing protocols that employ moderate concentrations (1.5 to 2.0 M) of penetrating cryoprotective agents (CPAs) such as dimethylsulfoxide (DMSO) (Whittingham et al. 1972), and (2) vitrification protocols that require rapid cooling rates and very high concentrations (i.e., 6-8M) of CPA mixtures (Rall & Fahy 1985). Although both methods have been improved over the years, several challenging problems, such as unsatisfactory overall success rates, reliability issues, CPA toxicity, biosafety and devitrification risks associated with vitrification techniques, and expensive containment cooled by liquid nitrogen ($LN_2$) for storage and transportation, remain.

In recent years, cell drying approaches such as freeze-drying and isothermal evaporative drying were also explored to store samples at ambient temperature (Wakayama & Yanagimachi 1998, Chen et al. 2001, Puhlev et al. 2001). The freeze-drying approach typically results in cell death, and hence can be used only for sperm storage because intracytoplasmic injection of even dead sperm can lead to healthy offspring (Wakayama & Yanagimachi 1998, Bhowmick et al. 2003). Although the isothermal evaporative drying can preserve membrane integrity of a small proportion of desiccated cells for a short time period, the recovered cells are severely compromised and not functional due to extended exposure to excessive osmotic stresses in the supersaturated rubbery region, where the evaporative drying is infinitely slow due to extremely increased viscosity.

Therefore it is an object of the invention to provide compositions and methods for improved biopreservation of cells and tissue.

It is another object of the invention to provide improved compositions and methods for germ cell preservation.

It is yet another object of the invention to provide a system for improved biopreservation of cells and tissues.

SUMMARY OF THE INVENTION

Methods and compositions are provided for the biopreservation of cells, tissues, organs, and animals. One embodiment provides a method that includes first desiccating cells sufficiently close to the $T_g$, for example until entering into the rubbery region, at a maximal rate that still allows the cells to equilibrate with the changing extracellular milieu, and then cooling the samples below $T_g$ to achieve a stable glassy state. The material to be preserved is dried in a desiccation medium.

In one embodiment, the desiccation medium contains sugars, polymers, and small amounts of a conventional CPA to obtain a glassy state at high subzero and suprazero temperatures and to minimize CPA toxicity.

In one embodiment the desiccation medium contains 0-90 mM NaCl (preferably 0-5 mM), 2-90 mM KCl (preferably 2-5 mM), 0.2-4 mM $KH_2PO_4$ (preferably 0.2-2 mM), 0.8-16 mM $K_2HPO_4$ (preferably 0.8-8 mM), 1-20 mM Na lactate (preferably 2-5 mM), 0.1-1 mM Na pyruvate (preferably 0.2-0.4 mM), 1-10 mM alanyl-glutamine (preferably 1-2 mM), 1-10 mM glycine (preferably 1-2 mM), 1-10 mM taurine (preferably 2-5 mM), 1-20 mM tricholine citrate (preferably 2-5 mM), 1-10 mM adenosine (preferably 2-5 mM), 0.05-0.5% EGTA (preferably 0.05-0.1 mM), 50-350 mM trehalose (preferably 150-200 mM), 0.1-0.5% albumin (preferably 0.4%), 5-20% maltodextrin (preferably 10%), 2-10% polyvinyl alcohol (preferably 3-5%), 1-10% ethylene glycol or propylene glycol (preferably 3-5%), 0.1-1 mM trolox (preferably 0.5 mM), 1× tempol, 0.5× essential amino acids, 0.5× non-essential amino acids, and 15-30 mM MOPSO or HEPES (preferably 20 mM). Trehalose can be replaced with other disaccharides such as sucrose and trisaccharides such as raffinose. Similarly, maltodextrin can be replaced/supplemented with other polymers such as polyvinylpyrrolidone, ficoll, hyaluronan, dextran, pentastarch or hydroxyethyl starch at similar concentrations.

Another embodiment provides a desiccation system that includes a custom-made small slide chamber with a precise temperature controller and controlled dry nitrogen flow. The desiccation rate can be changed by changing the desiccation temperature and the flow rate of dry nitrogen gas. The slide chamber is placed on a stage warmer with a precise temperature controller, and the temperature of the nitrogen gas is adjusted by circulating the gas in a copper coil immersed in a water bath set to desired temperature. A flowmeter is used to control and adjust the flow of the nitrogen gas. The drying temperature can be monitored using a thin thermocouple wire placed in the center of the desiccation droplet.

The disclosed compositions and methods (1) avoid excessive osmotic stresses by rapidly desiccating samples to the rubbery region and then crossing the Tg curve by subsequent cooling; (2) avoid cytoskeletal/spindle injury, chilling injury, CPA toxicity, and biosafety risks; (3) allow cost-effective long-term storage of samples at high subzero and suprazero temperatures, and hence facilitating transportation of the samples and cell-based therapies; and (4) avoid the edge-effect, by performing desiccation in a spherical droplet. The latter improves the desiccation outcome by permitting controlled and uniform desiccation patterns. Once optimized, the desiccated cooling method can be carried out under completely aseptic conditions using a semi-automatic robotic system, and thus solving the reliability and biosafety issues associated with the current protocols.

In summary, the proposed approach is biologically inspired and would not only overcome many limitations of currently used slow-freezing and vitrification protocols, but also pave the way for proper long-term storage and transportation of cells at ambient temperature to facilitate cell-based therapies.

DETAILED DESCRIPTION OF THE INVENTION

I. Definitions

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The initialism "CPA" refers to cryoprotective agent.

II. Compositions for Preservation

Cellular compositions can be preserved using the disclosed compositions and methods. The cellular compositions can be prokaryotic or eukaryotic. In one embodiment the cellular compositions are mammalian, for example human. In other embodiments, the cellular compositions are non-human.

A. Material to be Preserved

1. Cells

Typically, the materials that are preserved are cellular materials. The cells are preferably mammalian cells such as human cells, but can be from any animal, prokaryote, protist, or plant. One embodiment provides compositions and methods for biopreserving mouse or primate cells including human cells.

In another embodiment the material to be preserved is a gamete such as an ovum or sperm. In still another embodiment, the material is semen or spermatozoa. In still another embodiment, the material contains one or more oocytes for example MII oocytes. The cells can be haploid, diploid, or polyploid.

In another embodiment, the material to be preserved is an embryo or blastocyst, for example a human embryo or human blastocyst.

Suitable cells can be somatic cells, for example cells from tissues or organs of the body. Other cells that can be used with the disclosed compositions include, but are not limited to myeloid cells, lymphoid cells, hematopoietic cells, stem cells, and pluripotent cells. Myeloid cells include, but are not limited to monocytes, macrophages, neutrophils, basophils, eosinophils, erythrocytes, dendritic cells, and megakaryocytes or platelets. Lymphoid cells include, but are not limited to T cells, B cells, and natural killer cells. Stem cells include, but are not limited to adult stem cells, embryonic stem cells, hematopoietic stem cells, and mesenchymal stem cells or bone marrow stromal cells.

Stem cells are undifferentiated biological cells, which means that they are not specialized in any matter, but have the ability to differentiate into specialized cells, as well as divide and replicate to produce more stem cells. Embryonic stem cells are taken from blastocyst, an early-stage embryo usually at 4-5 days after fertilization. Markers for human embryonic stem cells include but are not limited to Oct4, Nanog, SOX2, SSEA4 and Tra-1-60. In one embodiment, the stem cells have one or more stem cell markers found at https://www.labome.com/method/Adult-Stem-Cell-and-Embryonic-Stem-Cell-Markers.html (which is incorporated by reference in its entirety).

Adult stem cells can be from brain, bone marrow, peripheral blood, blood vessels, umbilical cord blood, umbilical cord tissue, fat tissue, skeletal muscle, skin, teeth, heart, gut, liver, ovarian epithelium, and testis.

Progenitor cells can also be used with the disclosed compositions and methods. Progenitor cells are early descendants of stem cells that can differentiate to form one or more kinds of cells, but unlike stem cells, progenitor cells cannot divide and reproduce indefinitely.

2. Tissues

The material to be preserved can be cellular tissue. Preferred tissues are mammalian. The tissue can be derived from ectoderm, mesoderm, or endoderm. For example, the tissue can be ocular tissue, skin, muscle, alimentary tissue, brain, heart, lung, kidney, bladder, arterial, venous, and other tissues of the body. The tissue can be adult tissue or embryonic tissue.

3. Organs

In some embodiments, organs can be preserved using the disclosed compositions and methods. Preferred organs are mammalian organs. For example, an eye, heart, ovary, or kidney can be preserved, particularly if they are harvested from a juvenile organism.

4. Organisms

Smaller organisms can be preserved using the disclosed methods and materials. For example, bacteria, protists, nematodes, flatworms, zebra fish, and insects can be preserved using the disclosed methods and compositions.

B. Desiccation Medium

The material to be preserved is combined with a desiccation medium. In one embodiment the desiccation medium includes a sugar, buffered saline, and polymers and/or cryoprotective agents (CPAs).

1. Sugars

A preferred sugar is trehalose and can be used at concentrations of 50 to 350 mM. Trehalose is also known as mycose or tremalose. It is a natural alpha-linked disaccharide formed by an $\alpha,\alpha$-1,1-glucoside bond between two $\alpha$-glucose units.

Other sugars that can be used at similar concentrations, include but are not limited to disaccharides (e.g., sucrose, lactobionate, lactose, maltose, cellobiose) monosaccharides (e.g., galactose, glucose, fructose), and trisaccharides (e.g., raffinose, maltotriose).

The sugar can be present in about 0.1 to 0.2 M, preferably 0.15 M.

2. Polymers

A preferred polymer is maltodextrin and can be used at concentrations of 5 to 20% mM. Maltodextrin consists of D-glucose units connected in chains of variable length. The glucose units are primarily linked with $\alpha(1\rightarrow 4)$ glycosidic bonds. Maltodextrin is typically composed of a mixture of chains that vary from three to 17 glucose units long.

Other polymers that can be used alone or in combination at similar concentrations include, but are not limited to albumin, polyvinylalcohol, polyvinylpyrrolidone, ficoll, hyaluronan, dextran, pentastarch or hydroxyethyl starch.

3. Cryoprotective Agents

A preferred cryoprotective agent (CPA) is ethylene glycol and can be used at concentrations of 1 to 10%.

Other CPAs that can be used alone or in combination at similar concentrations include, but are not limited to propylene glycol, dimethylsulfoxide, glycerol, ectoine, and butanediol.

III. Methods of Preservation

A. Desiccation

The material to be preserved is combined with a desiccation medium and then desiccated. In a preferred embodiment, the material is desiccated using non-isothermal desiccation that involves drying of specimen to the so-called rubbery region and then cooling to cross the Tg curve. In one embodiment, the material is desiccated using a convective drying approach by purging dry nitrogen gas or similar inert gases at different temperatures followed with cooling.

Another form of convective drying that can also be used for our approach is desiccation of specimen using saturated salt solutions in sealed chambers. The saturated salt solutions include cesium fluoride (~3% equilibrium relative humidity), lithium bromide (~6% equilibrium relative humidity), zinc bromide (~7.7% equilibrium relative humidity), potassium hydroxide (~8.2% equilibrium relative humidity), and lithium chloride (~11% equilibrium relative humidity).

Other suitable methods of desiccation are known in the art. In one embodiment vacuum desiccation is used to desiccate the material. The vacuum desiccation involves decreasing the pressure around the material below the vapor pressure of water by applying vacuum. This results in increased evaporation rate as result of the decreased boiling point of water.

In another embodiment, convective desiccation is combined with freeze-drying that is also called "lyophilization". The freeze-drying process involves converting water to ice by cooling specimen, and then removing frozen water in two steps through sublimation (primary drying) and desorption (secondary drying) by applying vacuum and heat. In this embodiment, the initial convective desiccation is stopped at different moisture contents before reaching the rubbery region, and then the material is slowly cooled to different subzero temperatures (−20° C., −40° C. or −80° C.) to induce extracellular ice nucleation. Subsequently, freeze-drying of the material is performed without or with the secondary step to bring the specimen in a glass-like state at subzero or suprazero temperatures, respectively.

IV. Systems for Preservation

Figure 6:
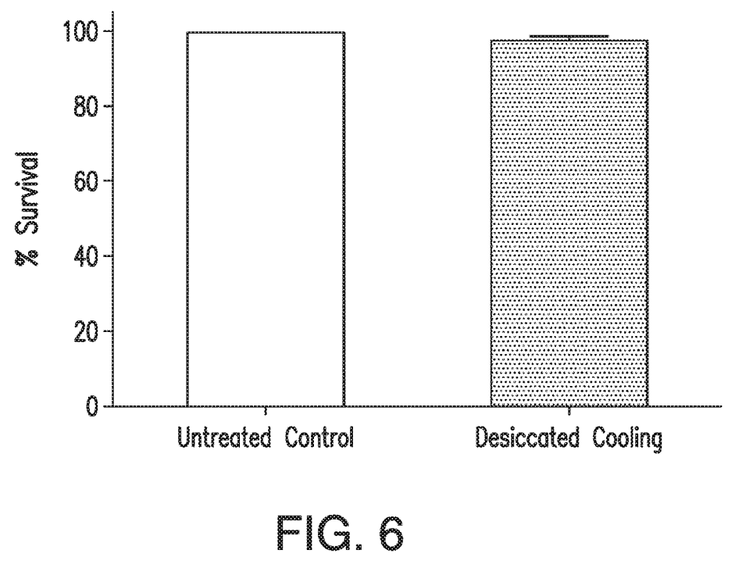
FIG. 6 is a bar graph of % Survival of mouse M II oocytes that were desiccated and subsequently cooled below Tg before warming and rehydration. The rates represent mean±SEM. No shading is untreated control. Stippled is desiccated cooling.
Figure 7:
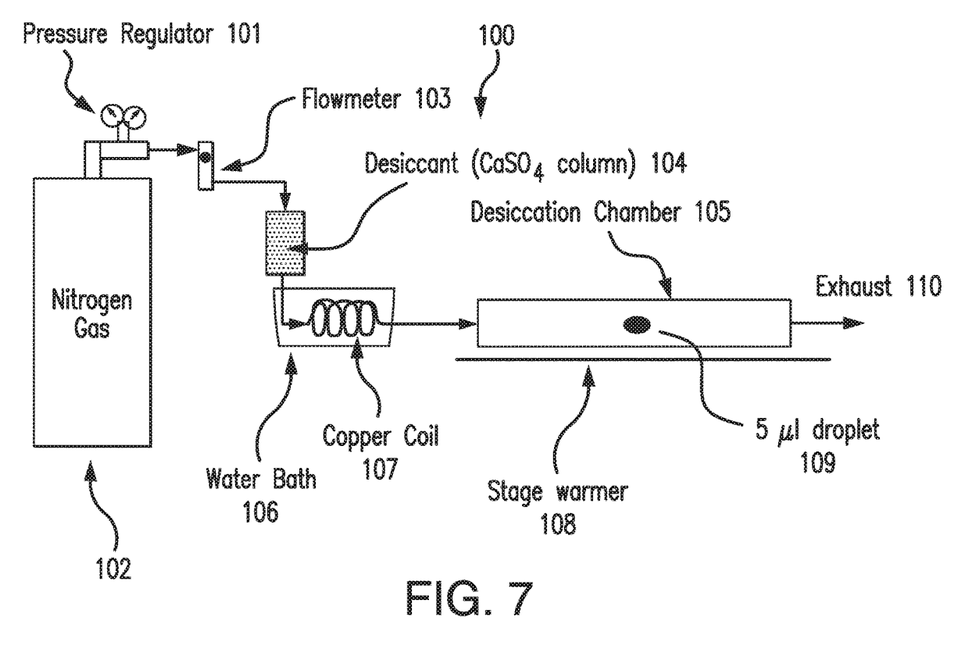
FIG. 7 is a diagram of an exemplary desiccation system 100.

FIG. 6 shows an exemplary desiccation system 100. System 100 is a convective desiccation system that includes a small slide chamber 105 with a material to be desiccated 109. Slide chamber 105 is placed on a precise temperature controller or stage warmer 108 and a controlled dry nitrogen flow flows from nitrogen gas container 102 through pressure regulator 101 and flow meter 103. The nitrogen gas then flows through desiccant 104 and copper coil (107) immersed in a water bath 106 into desiccation chamber 105 and out of desiccation chamber 105 as exhaust 110.

The drying rate can be changed by changing the drying temperature by changing (1) the temperature of water bath 106 and/or stage warmer 108 and (2) the flow rate of dry nitrogen gas using pressure regulator 101 and flow meter 103. The slide chamber 105 is placed on a stage warmer 108 to adjust the desiccation temperature along with adjusting the temperature of the nitrogen gas by circulating the gas in a copper coil 107 immersed in a water bath 106 set to desired temperature. The temperature of the copper coil and thus the flowing nitrogen gas is changed by heating or cooling the water bath. There are commercially available cooling and heating water baths (e.g., https://www.polyscience.com/products/circulating-baths/refrigerated-circulators) with precise temperature controller. A flowmeter 103 is used to control and adjust the flow of the nitrogen gas.

At the beginning of each experiment, the drying temperature is monitored and adjusted using a thin thermocouple wire placed in the center of the sample droplet.

EXAMPLES

Example 1: Desiccation Tolerance with Respect to Duration of Desiccation

Conventional isothermal desiccation exposes specimen to extreme osmotic and chemical stresses due to highly concentrated electrolytes in the rubbery region for long time periods, which results in loss of cell viability and functionality. In contrast, our invention involving non-isothermal desiccation (desiccated cooling) first brings specimen to the rubbery region and then into glassy state by fast desiccation and subsequent cooling, respectively, in a short time period. Consequently, our invention avoids exposing specimen to high osmotic and chemical stresses for extended periods. To demonstrate the beneficial effect of our concept, we desiccated mouse metaphase II (M II) oocytes to different moisture contents using fast and slow desiccation approaches that partially mimic our concept and isothermal desiccation, respectively. These experiments are described next.

Materials and Methods

A phosphate-buffered saline (PBS) containing 0.4% bovine serum albumin (BSA) was used as a starting desiccation medium based on its simple composition that was preferable to not complicate the experimental outcome due to components of a complex desiccation medium. Further, the objective of these experiments was to test the effect of the desiccation duration without bringing specimen into a glassy state.

Slow and fast desiccation are can be achieved by adjusting several variables (e.g., temperature and flow rate of dry nitrogen gas, temperature of stage warmer, droplet size, etc.). Slow and fast desiccation of M II oocytes were achieved by changing the flow rate of dry nitrogen gas using a flowmeter (Gilmont Instruments) while performing the experiments at ambient temperature.

The fast protocol required approximately 9 minutes to desiccate a sample to a residual moisture content of 5% while the same residual moisture content was obtained in ca. 20 minutes in the case of slow desiccation. After being randomly distributed into two groups (i.e., fast and slow desiccation) and desiccated to different moisture contents, M II oocytes were rehydrated by adding desiccation medium, and then cultured in Hypermedium (Eroglu et al., 2003 and 2009) at 37° C. for at least 2 hours before examining their post-rehydration survival. Hypermedium includes 95 mM NaCl, 4.78 mM KCl, 0.38 mM $KH_2PO_4$, 0.2 mM $MgSO_4$ $7H_2O$, 2.0 mM $CaCl_2$ $2H_2O$, 20 mM Na-lactate, 0.33 mM Na-pyruvate, 2.78 mM glucose, 1 mM glutamine, 0.03 mM EDTA, 4 mg/ml BSA, 50 mg/ml gentamycin, 50× essential amino acids (Gibco), 100× nonessential amino acids (Gibco), and either 15 mM HEPES or 25 mM $NaHCO_3$, depending on oocyte manipulations or culture, respectively with an osmolality of 280 to 360 mOsm.

The residual moisture content (% RM) of samples was determined gravimetrically using the following formula:

$$\% \text{ RM} = 100 \times (DW-BW)/(HW-BW)$$

where DW is the dehydrated weight of the sample after desiccation; BW is the baked weight of a comparable sample after heating in an oven at 90° C. for >24 h; and HW is the initial hydrated weight of the sample before desiccation. Experiments were repeated more than three times, and a total of 200 M II oocytes were used.

Results

Figure 1:
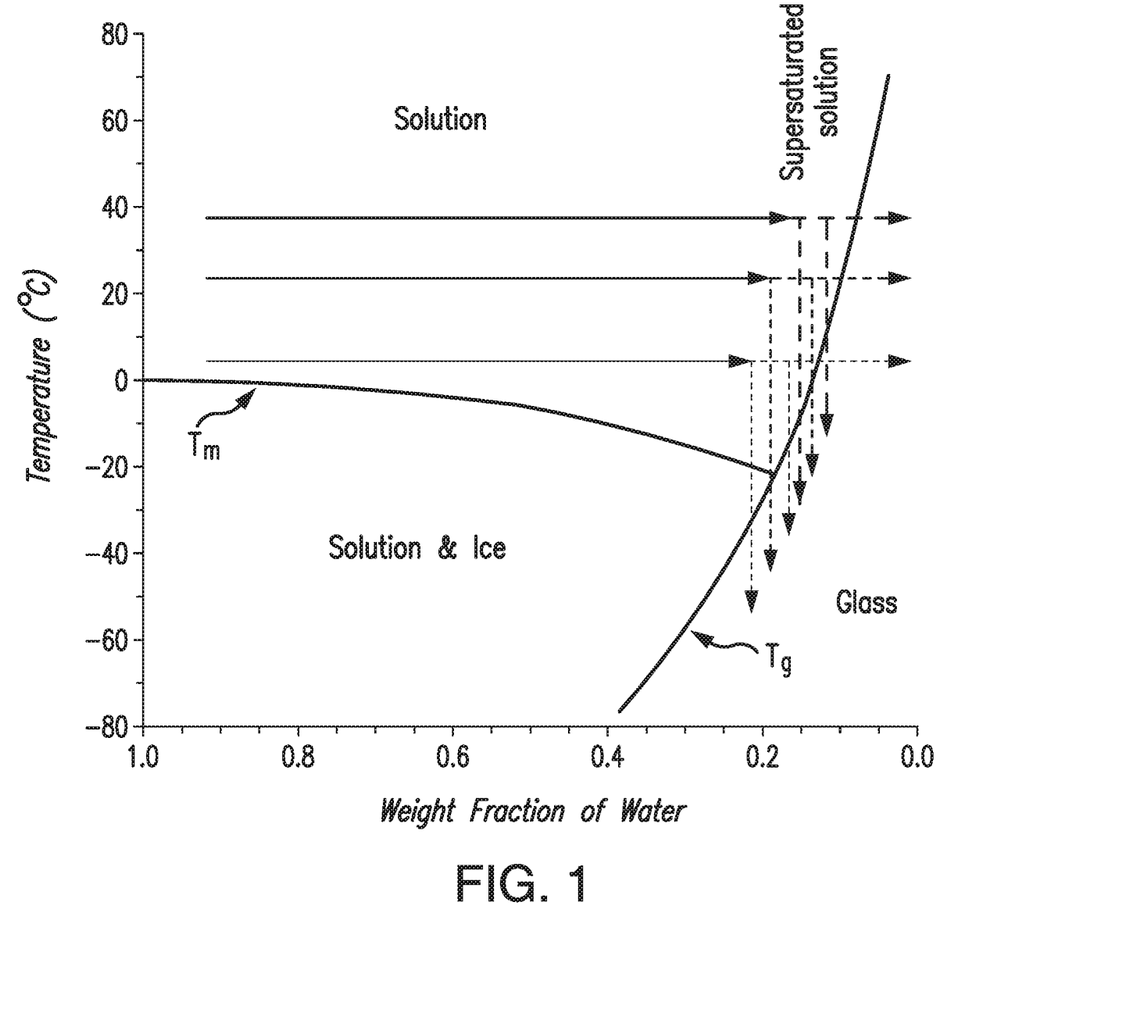
FIG. 1 is a line graph of Temperature (° C.) versus Weight Fraction of Water showing a trehalose phase diagram superimposed with hypothetical paths for desiccated cooling of cells. For simplicity, only 37° C., 23° C., and 4° C. are shown with a small number of cooling paths. Horizontal arrows extending beyond the Tg curve show isothermal drying paths while vertical arrows crossing the Tg curve represent some of the non-isothermal paths (desiccated cooling).
Figure 2:
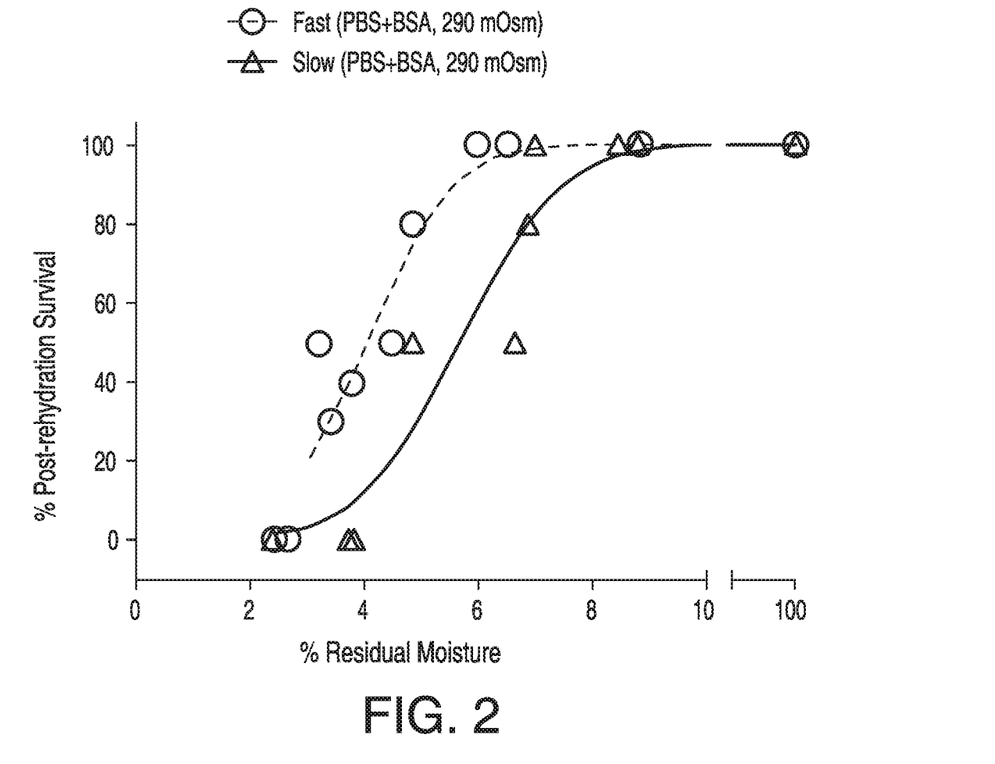
FIG. 2 is a line graph of % Post-rehydration Survival versus % Residual Moisture of mouse M II oocytes. The data points represent survival rates for individual samples containing approximately 10 oocytes each. (○) Fast desiccation (PBS+BSA, 290 mOsm); (Δ) Slow desiccation (PBS+BSA, 290 mOsm).

The results of these experiments are summarized in FIG. 2. When the fast desiccation protocol was used, M II oocytes tolerated desiccation stresses remarkably well. The post-rehydration survival remained close to 100% down to 5% residual moisture, and then declined between 5 and 3% residual moisture content. In the case of slow desiccation, the post-rehydration survival decreased at a higher residual moisture content (≥6%) indicating that prolonged exposure to osmotic and chemical stresses adversely affects the desiccation tolerance of mouse M II oocytes. It is important to note that the slow desiccation approach used in these experiments is still considerably faster than typical isothermal drying. These findings support the concept that a fast desiccation strategy with subsequent cooling (non-isothermal desiccation) can minimize osmotic injuries and safely bring oocytes below the glass transition temperature, as opposed to isothermal drying, which exposes samples to extreme osmotic stresses in the rubbery region for extended time periods.

Figure 3:
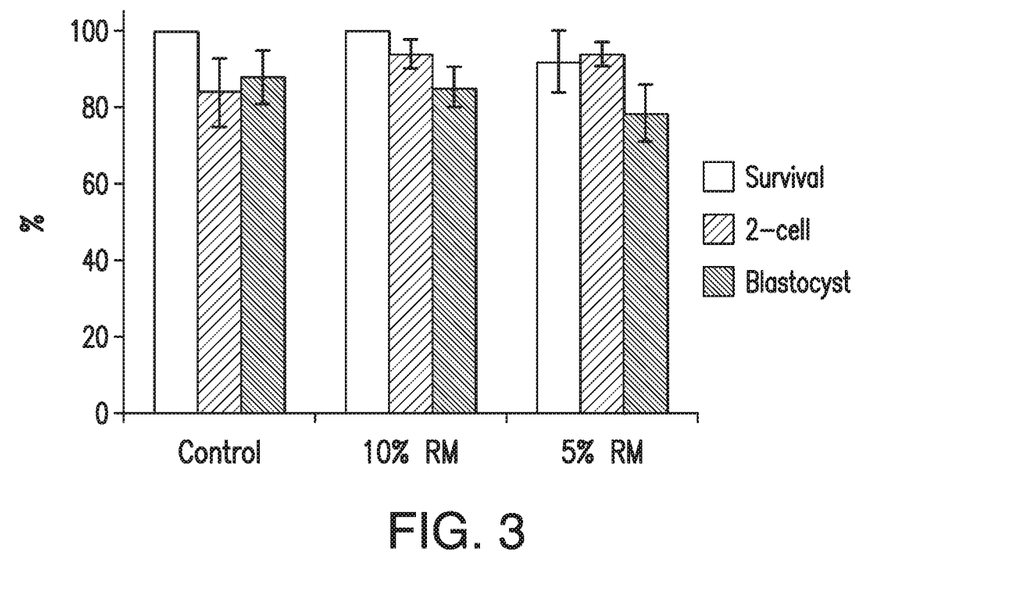
FIG. 3 is a bar graph of % survival, fertilization, and embryonic development rates of M II mouse oocytes desiccated to 10% or 5% residual moisture (RM). The rates represent mean±SEM involving a total of 121 oocytes. (white bar) survival, (wide hatched bar) 2-cell, and (narrow hatched bar) blastocyst.

Next, fertilization and embryonic development competence of desiccated oocytes were examined with respect to untreated controls. Oocytes desiccated to either 5% or 10% residual moisture were rehydrated, and then inseminated. As shown in FIG. 3, the post-rehydration survival, fertilization and embryonic development rates for both residual moisture contents were comparable to those of untreated controls, without any significant difference. Taken together, this data show that M II oocytes tolerate desiccation induced osmotic stresses remarkably well.

Example 2: Desiccation Tolerance in the Presence of Trehalose

Trehalose is an important component of the desiccation medium. This particular set of experiments was carried out to examine how extracellular trehalose affects desiccation behavior of mammalian oocytes.

Materials and Methods

A total of 250 mouse M II oocytes were subjected to fast and slow desiccation as described earlier. The desiccation medium was again PBS plus 0.4% BSA but supplemented with 0.15 M trehalose. However, PBS was diluted with ultrapure water such that upon addition of 0.15 M trehalose, the total osmolality of the medium remained isotonic (i.e., 290 mOsm/kg). After desiccation to different moisture contents, the oocytes were rehydrated by adding desiccation medium, and then cultured in Hypermedium for ≥2 hours. Subsequently, viability of the desiccated oocytes was examined.

Results

Figure 4:
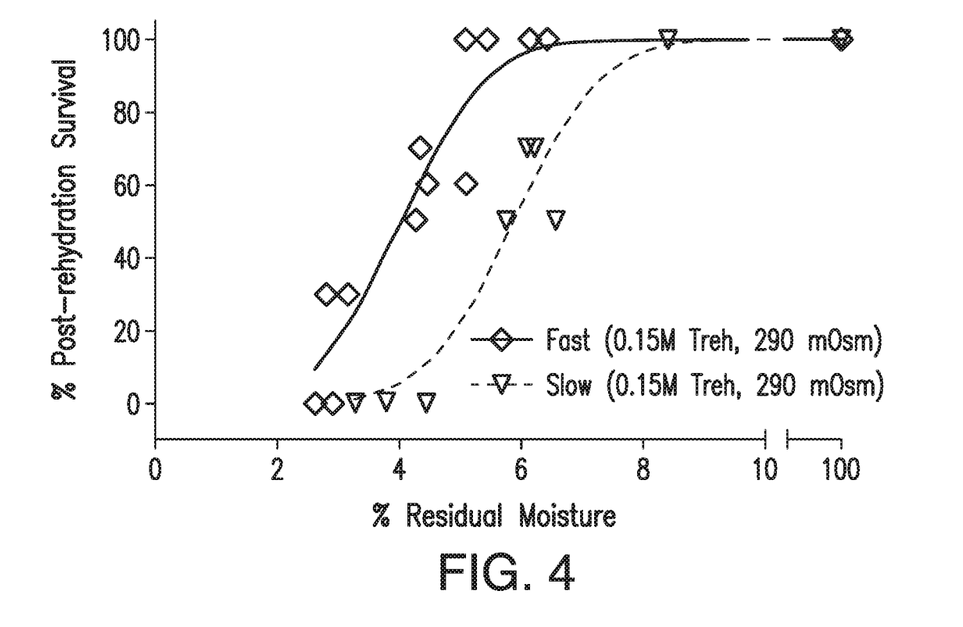
FIG. 4 is a line graph of Post-rehydration Survival versus % Residual Moisture for mouse M II oocytes after desiccation in the presence of 0.15 M extracellular trehalose. Symbols represent survival rates for individual samples containing 10 oocytes each. A nonlinear least squares curve fitting was performed to fit the data. (◇) Fast desiccation (0.15M Treh, 290 mOsm); (▽) Slow desiccation (0.15M Treh, 290 mOsm).

The results of these experiments are summarized in FIG. 4. Consistent with the previous results, the fast desiccation approach yielded better results in terms of retaining cell viability at low residual moisture down to around 4%. In contrast, the survival rate steeply declined around at 6% residual moisture when MII oocytes were exposed to desiccation stresses for an extended period as a result of slow desiccation. These results further support the concept and also suggest that trehalose supplementation improves the desiccation tolerance.

Example 3: Effect of Initial Salt Concentrations on Desiccation Tolerance

Desiccation of a cell suspension results in dramatically increased salt concentrations that do not raise the glass transition temperature (Tg) of a given desiccation medium but can impair cell viability and function. It might be possible to partially reduce the desiccation-induced osmotic and chemical stresses by lowering initial salt content of a desiccation medium while partially compensating it with an organic osmolyte and good glass former such as trehalose. If it holds true, this would also support our concept while adding a novel aspect to our desiccation medium.

Materials and Methods

To test the idea mentioned above, 0.15 M trehalose was added to undiluted and diluted PBS solutions such that the salt content of PBS either remained unchanged or reduced to two different degrees with resulting total osmolalities of 425, 290, and 200 mOsm/kg, respectively. Based on our previous results, the fast desiccation approach was used to desiccate a total of 391 MII oocytes to various residual moisture contents.

Results

Figure 5:
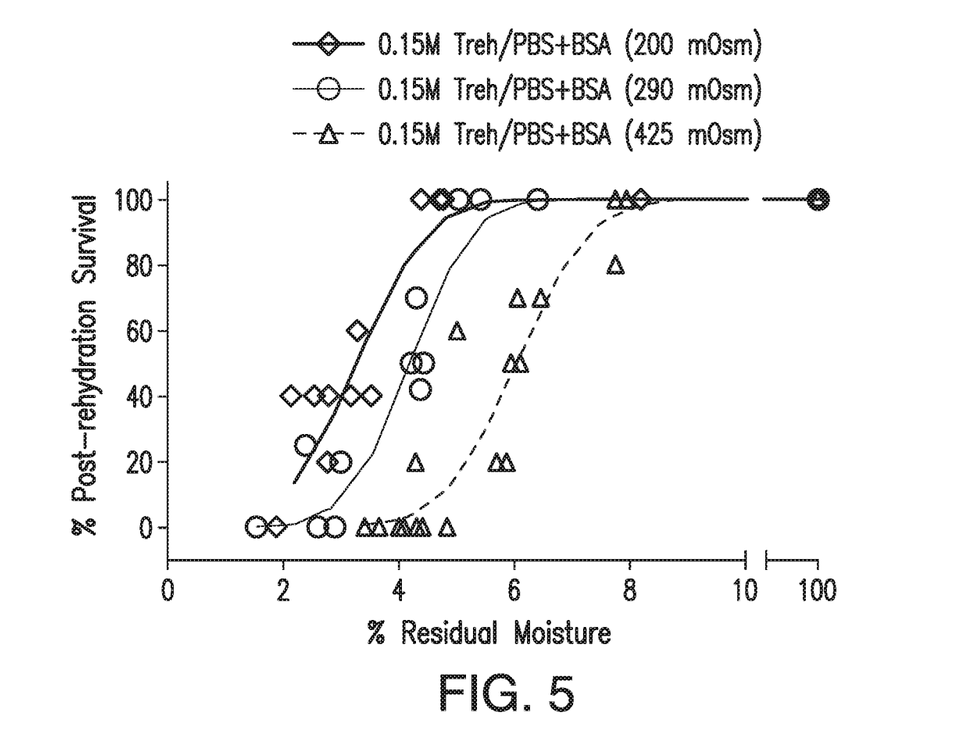
FIG. 5 is a line graph of Post-rehydration Survival versus % Residual Moisture for mouse M II oocytes after desiccation in the presence of progressively lowered initial salt content, which compensated with 0.15 M trehalose. Symbols represent survival rates for individual samples containing up to 10 oocytes each. A nonlinear least squares curve fitting was performed to fit the data. (◇) 0.15M Treh/PBS+BSA (200 mOsm); (○) 0.15M Treh/PBS+BSA (290 mOsm); (Δ) 0.15M Treh/PBS+BSA (425 mOsm).

As shown in FIG. 5, the desiccation tolerance of MII oocytes is progressively improved with decreasing salt content of the medium. These results support our concept and show that there is a negative correlation between the initial high salt content of a desiccation medium and desiccation tolerance. Therefore, we claim a desiccation medium with minimal salt content, which is compensated with good osmolytes and glass formers such as trehalose, taurine, glycine, glutamine, choline, lactobionate, maltodextrin, and pentastarch.

Example 4: Desiccated Cooling of Mouse and Human Oocytes

Materials and Methods

To further test the concept, a model sugar (0.15 M trehalose), a sugar polymer (12% maltodextrin), a synthetic polymer (3% PVA), and small amounts (5%) of a conventional CPA (ethylene glycol) were added to the desiccation medium and then mouse oocytes were desiccated to the rubbery region before bringing them below Tg and thus into a glass-like state by subsequent cooling. The Tg of this desiccated medium is estimated to be between −20° C. and −40° C. To demonstrate the transition into a glassy state and thus the absence of any ice formation during this process, the samples were cooled to liquid nitrogen ($LN_2$) temperature (−196° C.) and held there at least for 5 minutes. Subsequently, the samples were warmed up and rehydrated to evaluate survival of the oocytes. These experiments were repeated at least three times and a total of 180 M II oocytes were used.

Results

As shown in FIG. 6, almost all (97.4%) oocytes survived desiccation and subsequent cooling below Tg, clearly supporting the concept.

The same experiments were also repeated using a small number (10) of discarded failed-to-fertilize human oocytes. On average, approximately 88% of human oocytes survive the desiccated cooling to the LN2 temperature (Table 1).

TABLE 1

Survival of discarded failed-to-fertilize human oocytes after desiccated-cooling and rehydration.

| | No. of oocytes used | No. of intact oocytes after rehydration | % Survival |
| --- | --- | --- | --- |
| Experiment 1 | 3 | 3 | 100 |
| Experiment 2 | 2 | 2 | 100 |
| Experiment 3 | 4 | 2 | 50 |
| Experiment 4 | 1 | 1 | 100 |
| Total | 10 | 8 | 87.5* |

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

I claim:

1. A method for preserving a biological sample comprising: transferring the biological sample to be preserved comprising one or more cells to a desiccation medium, wherein the desiccation medium comprises trehalose at a concentration of 0.05-0.30, a polymer at a concentration of 5-20%, and a cryoprotective agent at a concentration of 1 to 10%; desiccating the biological sample in the desiccation medium sufficiently close to the glass transition temperature (Tg) until entering into the rubbery region while allowing the biological sample to equilibrate to changing extracellular conditions during desiccation; and crossing the Tg curve of the biological sample by cooling the desiccated biological sample to 10° C. or more below the Tg of the biological sample to achieve a glassy state of the biological sample.

2. The method of claim 1, wherein desiccation of the biological sample takes place in a spherical droplet of the desiccation medium to achieve a uniform drying.

3. The method of claim 1, wherein the desiccation medium replaces a portion of salts with osmolytes or glass formers to reduce both osmotic and chemical stresses while raising the Tg of the biological sample.

4. The method of claim 1, wherein desiccating the biological sample comprises convective or evaporative or vacuum desiccation while raising the Tg.

5. The method of claim 4, wherein an initial desiccation of the biological sample is stopped at different moisture contents of the biological sample before reaching the rubbery region, and then the initially desiccated biological sample is cooled to different subzero temperatures selected from the group consisting of 20° C., −40° C. and −80° C. to induce extracellular ice nucleation.

6. The method of claim 5, further comprising freeze-drying biological sample resulting from claim 5, which results in crossing the Tg curve of the biological sample at subzero or suprazero temperatures.

* * * * *